United States Patent [19]

Wheeler et al.

[11] Patent Number: 5,380,538
[45] Date of Patent: * Jan. 10, 1995

[54] CRYSTAL MODIFIERS FOR DIACETIN FATS

[75] Inventors: Edward L. Wheeler, Fairfield; Michael S. Otterburn, Randolph, both of N.J.

[73] Assignee: Nabisco, Inc., Parsippany, N.J.

[*] Notice: The portion of the term of this patent subsequent to Nov. 2, 2010 has been disclaimed.

[21] Appl. No.: 991,688

[22] Filed: Dec. 16, 1992

Related U.S. Application Data

[63] Continuation-in-part of Ser. No. 804,140, Dec. 6, 1991, Pat. No. 5,258,197, and Ser. No. 732,518, Jul. 19, 1991, abandoned, which is a continuation-in-part of Ser. No. 555,902, Jul. 20, 1990, abandoned, and Ser. No. 624,056, Dec. 7, 1990, abandoned, said Ser. No. 804,140, is a continuation-in-part of Ser. No. 624,056, Dec. 7, 1990, which is a continuation-in-part of Ser. No. 410,161, Sep. 20, 1989, abandoned.

[51] Int. Cl.$^6$ .......................... A23P 1/08; A23D 9/06
[52] U.S. Cl. ..................................... 426/99; 426/660; 426/804
[58] Field of Search ............... 426/601, 607, 660, 804, 426/99

[56] References Cited

U.S. PATENT DOCUMENTS 2,615,160 10/1952 Baur .
3,192,057 6/1965 Hines et al. .
3,388,085 6/1968 Levkoff et al. .
5,258,197 11/1993 Wheeler .............................. 426/607

OTHER PUBLICATIONS

Shishikura 1986 Agric Biol Chem 50(5) 1209-1215.
Alikonis, J. J., Candy Technology, AVI Pub. Co., Westport, Conn. (1979) p. 46.
Bailey's Industrial Oil and Fat Products, 4th ed., vol. 1, John Wiley & Sons, New York, (1979) pp. 322-327.
Bonanome, A. and Grundy, S. M., New Eng. Jour. Med. 318: 1244-1248 (1988).
Feuge, R. O., Food Technology 9: 314-318 (1955).
Feuge, R. O., et al., J. Amer. Oil Chem. Soc. 29: 11-14 (1952).
Mattson, F. H., et al., J. Nutr. 59: 277-285 (1956).
Mensink, R. P. and Katan, M. B., New Eng. Jour. Med., 323: 439-445 (1990).

*Primary Examiner*—Carolyn Paden

[57] ABSTRACT

The physical properties of diacetin fats such as diacetopalmitin, diacetostearin, and diacetoarachidin, diacetobehenin are modulated by mixing them with about 10% to about 16% crystal modifier fats that are triglycerides bearing one short $C_2$ to $C_4$ acid residue and two long, saturated $C_{16}$ to $C_{22}$ fatty acid residues per molecule. The modified diacetin fats, which exhibit improved snap, gloss, hardness, bloom resistance, and mold release, are suitable for use in edible coatings, especially confectionery coatings.

24 Claims, 5 Drawing Sheets

CRYSTAL MODIFIERS FOR DIACETIN FATS

RELATED U.S. APPLICATION DATA

This is a continuation-in-part of co-pending U.S. application Ser. No. 07/804,140, filed Dec. 6, 1991, now U.S. Pat. No. 5,258,197 hereby incorporated in its entirety by reference, which was a continuation-in-part of U.S. application Ser. No. 07/624,056, filed Dec. 7, 1990, now abandoned, which was a continuation-in-part of U.S. application Ser. No. 07/410,161, filed on Sep. 20, 1989, now abandoned.

This is also a continuation-in-part of co-pending U.S. application Ser. No. 07/732,518, filed Jul. 19, 1991, hereby incorporated in its entirety by reference, which was a continuation-in-part of U.S. application Ser. No. 07/555,902, filed Jul. 20, 1990, now abandoned, and above-mentioned U.S. application Ser. No. 07/624,056, filed Dec. 7, 1990, now abandoned.

DESCRIPTION

TECHNICAL FIELD

This invention relates to a new class of crystal modifiers that improve the crystal structure and the palatability of confectioners' coatings made with acetoglycerides.

Because cocoa butter is hard and nongreasy at ordinary temperatures, with a melting point below the temperature of the human body, it is preeminently suitable for a coating fat for confections. Cocoa butter is brittle below about 27° C.; slightly above this temperature it softens and melts. The melting point of cocoa butter depends on the crystal modification in which it exists. A sample that has been quickly chilled solidifies to an unstable crystal form which liquefies if suddenly heated to a temperature as low as 20° to 25° C. However, if heating is carried out gradually, to permit transformation of the fat to its highest melting form, the melting point is usually about 35° to 36° C. (for a brief review, see Bailey's Industrial Oil and Fat Products, 4th ed., vol. 1, John Wiley & Sons, New York, 1979, pages 322 to 327).

The polymorphism of cocoa butter is quite complex, and is in part responsible for the unique melting behavior of the fat. Since cocoa butter can solidify in various crystalline forms, desirable gloss, bloom resistance, and acceptable melting characteristics are observed when the crystalline forms are stable, and these are generally achieved by careful tempering of the fat.

Many fats, including cocoa butter, form "alpha" crystals when they are rapidly cooled from a melt. Such crystals are characteristically a loosely packed, extended network of molecules that are thermodynamically unstable and tend to convert to more stable beta prime or beta forms that are more closely packed. Confectionery fats having more stable crystal forms are prepared by controlling cooling and/or tempering, and by adding small quantities of crystal modifiers.

Crystal modifiers such as, for example, sorbitan fatty acid esters, ethoxylated sorbitan fatty acid esters, mono- and di-glycerides, acetylated tartaric acid esters of monoglycerides, sucrose and citric acid esters, and lecithin, can retard the hardening rate, check the loss of gloss and the formation of bloom, reduce panning time, improve palatability and appearance, control crystallization and stabilize mixtures of confectionery fats (Alikonis, J. J., Candy Technology, AVI Pub. Co., Westport, Conn. 1979, page 46). A major commercial use of lecithin is to control viscosity in chocolate coatings, and when used in concentrations of about 0.3 to 0.5%, it minimizes the amount of cocoa butter needed in chocolate and improves the quality of candy products (id., page 47).

It would be desirable to further reduce or eliminate the amount of cocoa butter in confectionery products because it is expensive and ordinarily requires tempering under controlled conditions. It would also be desirable to prepare confectionery fats using acetoglycerides, which have recently been shown to be low in calories (co-pending U.S. application Ser. No. 07/804,140, cited above).

BACKGROUND ART

During the 1950's some fats were prepared by substituting acetic acid for a portion of the fatty acids occurring in ordinary fats or oils, thus producing what were then named "acetoglycerides" (Feuge, R. O., Food Technology 9: 314–318 (1955)). Feeding studies indicated that the nutritive value of mono- and diacetin fats were essentially the same to animals as those fed the corresponding conventional triglycerides (Mattson, F. H., et al., J. Nutr. 59: 277–285 (1956)).

Acetostearins are waxy fats having high, sharp melting points, limiting their applications in food products. One study described the fats as "highly flexible" and elastic; at a temperature of 22° C., they could be stretched more than 800% (Feuge, R. O., et al., J. Amer. Oil Chem. Soc. 29: 11–14 (1952)). When chewed in the mouth, diacetostearin has been described as "somewhat like a gum" (U.S. Pat. No. 2,615,160 to Baur, column 7, line 55). Though initially suggested for a variety of edible products, including coatings and possibly chocolate coatings, as well as in icings and frostings, as spray oils for crackers, as edible "beeswax" for synthetic honey, as an edible chewing gum base, and as protective coatings for products such as fruits, cheese, preserves, and meats (U.S. Pat. No. 2,615,160 to Baur, column 7, lines 59 to 64), the disclosures did not provide products with the functionality required for quality confectionery fats.

The diacetostearin of U.S. Pat. No. 2,615,160 is waxy and rubbery, so it is unacceptable for use as a confectionery coating, and acetodistearin tends to bloom and is also waxy. Instead of stretching, quality confectionery coatings and chocolates should have snap. Quality confectionery coatings also melt in the mouth without waxiness and preferably exhibit some glossiness. Preferred confectionery products contract on cooling to facilitate demolding. Dull, waxy diacetosterins are difficult to demold and so they do not exhibit these desirable properties.

Thus, in the intervening decades, waxy acetoglycerides have been primarily used, not as confectionery fats, but as protective coatings, thin films, moisture barriers and plasticizers. Some compositions of this nature are referred to as "hot melts" and may contain antibiotics (U.S. Pat. No. 3,192,057 to Hines and Shirk) or polymeric materials (U.S. Pat. No. 3,388,085 to Levkoff and Phillips) to prolong the life of the coating.

Recent research in this laboratory has shown that acetoglycerides bearing long ($C_{16}$ to $C_{24}$), saturated pendant groups such as the acetostearins are low in calories (U.S. application Ser. No. 07/804,140, cited above). Therefore, it would be desirable to have crystal modifiers that modulate the waxy, rubbery properties of acetoglycerides, especially diacetostearin, so that these fats can be employed in confectionery coatings.

DISCLOSURE OF THE INVENTION

An object of the present invention is to provide ways to modulate the properties of diacetin fats such as diacetostearin so the fats can be employed in confectionery coatings such as chocolate coatings.

It is a further and principal object of the present invention to provide crystal modifiers for diacetin fats.

It is another object of the invention to provide confectionery products coated with low calorie acetoglyceride coatings that demold easily and that have snap, hardness and gloss without waxiness and rubberiness.

These and other objects are accomplished by the present invention, which provides crystal modifiers for the diacetin fats diacetopalmitin, diacetostearin, diacetoarachidin, diacetobehenin, and mixtures of these. The crystal modifiers are acetylated, propylated, and butylated long chain, saturated diglycerides, i.e., triglycerides bearing one $C_2$ to to $C_4$ short acid residue and two long $C_{16}$ to $C_{24}$, preferably $C_{18}$ to $C_{22}$, saturated fatty acid residues.

Denoting the short moiety as S and the long as L, preferred confectionery coatings of this invention contain a sweetener, a flavor, and a fat ingredient comprising about 70% to 95%, more narrowly about 83% to about 90%, of a diaceto glyceride and about 5% to 30%, more narrowly about 10% to about 16%, of a SLL/LSL crystal modifier fat. In one especially preferred embodiment, the coating fat comprises diacetostearin containing about 10% to about 18% acetodistearin.

Confectionery coatings prepared with the improved diacetin fats of this invention are disclosed. These coatings exhibit good snap, hardness and gloss and demold easily, yet are lower in calories than typical confections prepared with conventional fats such as cocoa butter. Moreover, coatings made with the fat compositions of this invention exhibit bloom resistance and eliminate the need for tempering.

Methods for modifying the crystal structure of diacetostearins are also disclosed.

BEST MODE FOR CARRYING OUT THE INVENTION

Figure 1:
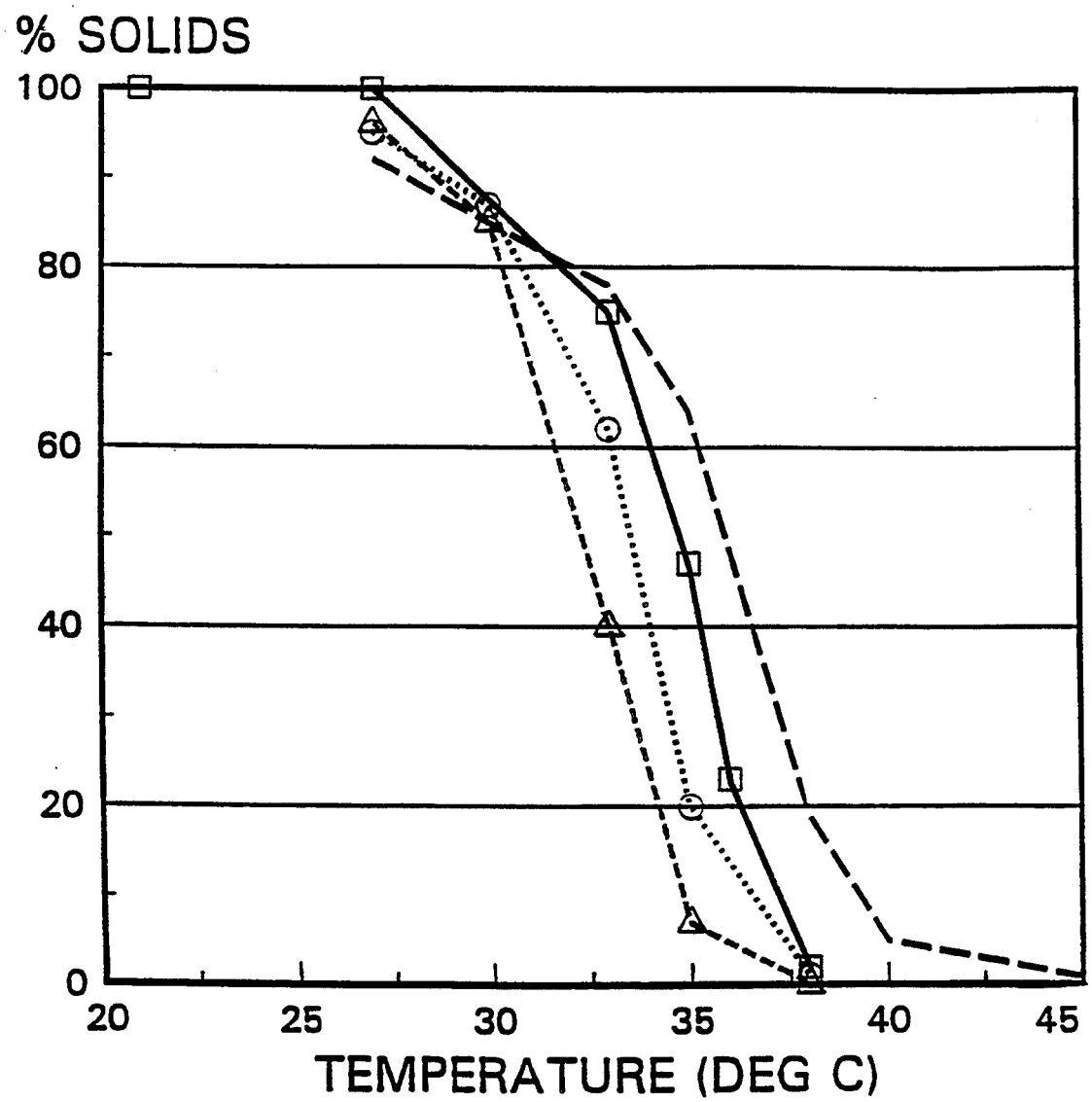
FIG. 1 shows differential scanning calorimetric (DSC) solid fat indices of freshly made confectioners' coatings prepared using diacetcstearin containing 3% acetodistearin (---△---), diacetostearin containing 13% acetodistearin (·····⊙·····), and diacetostearin containing 30% acetodistearin (-- -- --) compared with a control coating prepared using tempered cocoa butter (----☐----).

In the practice of this invention, the physical properties of diacetin fats are modified by admixing them with about 10 to about 18 weight % of a crystal modifying fat comprising triglycerides bearing one short $C_2$ to $C_4$ acid residue and two long, saturated $C_{16}$ to $C_{24}$, preferably $C_{18}$ to $C_{22}$, fatty acid residues per molecule. Mixtures of the crystal modifying fat with the diacetin fat yield a coating fat having desirable properties for confections.

By the term "diacetin fat" is meant fats bearing two acetic acid residues and one long, saturated $C_{16}$ to $C_{24}$ fatty acid residue per molecule. Diacetin fats can be triglycerides having the acetyl residues on the 1- and 2-positions or on the 1- and 3-positions, or a mixture of these. Example diacetin fats include diacetopalmitin (diacetylpalmitoyl glyceride), diacetostearin (diacetylstearoyl glyceride), diacetoarachidin (diacetyl-arachidoyl glyceride), diacetobehenin (diacetyl-behenoyl glyceride), and mixtures of these. Preferred diacetin fats contain at least about 75% diacetostearin, preferably at least about 85% diacetostearin.

Crystal modifying fats are triglycerides bearing one short $C_2$ to $C_4$ acid residue and two long, saturated $C_{16}$ to $C_{24}$, preferably $C_{18}$ to $C_{22}$, fatty acid residues per molecule. Denoting the short residue as "S" and the long as "L", the crystal modifying fats are either LLS or LSL species or a mixture of LLS and LSL species described by the following formulae:

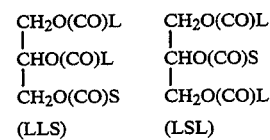

where each L, independently, is a long chain saturated aliphatic group having between 15 and 21 carbons, derived from a fatty acid having 16 and 24 carbons; and each S, independently, is a short chain group having 1 to 3 carbons, derived from an acid having 2 to 4 carbons.

Crystal modifying fats may also contain from 0 to 5%, more narrowly about 1 to about 3%, LLL.

Short acid residues have 2 to 4 carbons. Short residues are derived from carboxylic acids of the formula SCOOH, where S is a short chain aliphatic group having 1 to 3 carbons. As denoted herein, where triglycerides are described as bearing pendant groups derivied from acids having 2, 3, or 4 carbons, compositions derived from acids having predominantly 2, 3, or 4 carbons are inclucled. Acylation of a glycerol hydroxyl by acid SCOOH results in the attachment of short chain S to the glycerol backbone by means of an ester linkage (—O—(CO)—). Where there is more than one short group attached to a glyceride, the groups may be the same or different. As used herein, the term "acid residue" refers to an acyl group comprising a short chain portion, here S, and a carbonyl group.

Short chain S may be straight or branched. Short chain S may be derived from any synthetic or natural organic acid including, but not limited to acetic (ethanoic), propionic (propanoic), butyric (butanoic), and the like acids. As used herein, chemical names include isomeric variations; for example, "butyric acid" includes normal-butyric acid (butanoic) and iso-butyric (2-methylpropanoic) acid, and so forth. Preferred acids are acetic, propionic, and butyric acids, and mixtures of these.

The long saturated pendant groups are derived from fatty acids of the formula LCOOH, where L is a saturated aliphatic group having 15 to 23 carbons. L groups may be derived from any synthetic or natural, straight or branched saturated organic acid including, but not limited to, palmitic (hexadecanoic), stearic (octadecanoic), arachidic (eicosanoic), behenic (docosanoic), and the like acids. L groups may also be derived by hydrogenating unsaturated acids of the formula UCOOH, where U is a $C_{15}$ to $C_{19}$ unsaturated group, including, but not limited to, palmitoleic (9-hexadecenoic), oleic (cis-9-octadecenoic), vaccenic (trans-11-octadecenoic), linoleic (cis, cis-9,12-octadecedienoic), linolenic (9,12,15-octadecatrinoic and 6,9,12-octadecatrienoic), eleostearic (9,11,13-octadecatrienoic), arachidonic (5,8,11,14-eicosatetraenoic), and the like acids.

The various L and U groups can be derived from mixtures of fatty acids obtained from natural oils such as soybean, safflower, sunflower, sesame, peanut, corn, olive, rice bran, mustard seed, cottonseed, poppyseed, rapeseed, marine, meadowfoam and the like oils; fats such as babassu nut oil, palm oil, palm kernel oil, tallow, lard, shea butter, dairy butter; or plant waxes such as jojoba. Fat mixtures and/or fractions, crystallized fats, interesterified fats and mixtures of these may also be employed.

Especially preferred crystal modifying fats include acetodistearin (acetyl-distearoyl glyceride), propiodistearin (propionyl-distearoyl glyceride), butyrodistearin (butyro-distearoyl glyceride), and mixtures of these. Thus, where natural oils are employed as a source of L groups, hydrogenated fats having at least about 70%, preferably at least about 80%, stearic acid residues such as, for example, hydrogenated peanut oil, hydrogenated olive oil, hydrogenated soybean oil, hydrogenated sesame oil, and hydrogenated corn oil are especially desirable. Other embodiments employ L moieties derived from hydrogenated fats having at least about 90% stearic acid residues, such as hydrogenated sunflower oil, hydrogenated safflower oil and hydrogenated canola.

Diacetin and crystal modifying fats for coatings may be prepared using synthetic procedures known to those skilled in the art, such as, for example, directly esterifying glycerol or glycerol esters with fatty acids, fatty acid halides (notably chlorides) or fatty acid anhydrides, or transesterifying glycerol with fatty acid esters. The diacetin and crystal modifying fats are then mixed together.

Alternatively, a coating fat mixture comprising about 70% to about 95%, more narrowly about 83% to about 90%, of a diacetin fat and about 5% to about 30%, more narrowly about 10% to about 16%, of a crystal modifying fat may be prepared by interesterifying long chain triglycerides with triacetin for such time and under such conditions that triglycerides bearing long and short residues form. Because of limited solubility of triacetin in hydrogenated oils, a solvent is employed in one embodiment. Since the use of solvents is not preferred for the preparation of fats for edible coatings, however, a preferred synthesis is a single phase interesterification between a liquid feedstock oil and triacetin, followed by hydrogenation.

Starting materials for triglyceride preparations may be obtained commercially or isolated from natural sources. Alternatively, component triglycerides may be isolated from natural or processed fats or oils, or fractions thereof. Isolated or prepared triglycerides are purified using techniques known to those skilled in the art. These include, but are not limited to, steam deodorization, fractional crystallization, distillation, chromatography, and the like. Example purifications are illustrated hereafter.

Diacetin fats and crystal modifying fats may be incorporated into coating compositions as the sole fat ingredient, or in combination with another fat and/or fat mimetic. Other fats include butter, cocoa butter, natural triglycerides rich in highly desirable or essential fatty acids, such as oleic, linoleic, linolenic, or eicosapentaenoic acid, triglycerides bearing fatty acids having beneficial attributes such as those associated with conjugated linoleic acid isomers, medium chain triglycerides and the like. Other fat mimetics include any heretofore suggested as edible fat replacements, including, but not limited to, sugar esters, neoalkyl esters, polyglycerol esters, malonate esters, propoxylated glycerols, retrofats, carboxy/carboxylates, polyvinyl alcohol esters and the like.

When employed either alone or in products with other fats, the diacetin fat and crystal modifying fat mixture (hereinafter referred to as "modified diacetin fat") is desirably added to the coating composition in amounts effective to reduce the calories in the coating. For example, a 25% or greater replacement of the usual fat component can be effective for this purpose, and replacements of at least 50% are desired in many cases. An especially preferred embodiment employs the modified diacetin fat as at least about 90% of the fat ingredient in the food product, or, in another embodiment, as the only fat ingredient.

In chocolate-like coatings, modified diacetin fats are also employed in amounts effective to reduce bloom, i.e., in amounts that reduce visually apparent bloom at least about 35%, preferably at least about 50%. Preferred embodiments reduce visually apparent bloom by at least about 90% over two or three temperature (warming and cooling) cycles. As is familiar to the skilled artisan, bloom is a separation of fat crystals from the matrix of a chocolate coating, generally caused by separation of cocoa butter from the matrix and extrusion or recrystallization of fat to or on the surface, forming white layers or splotches. Bloom is usually ascribed to partial liquefication (due, for instance, to temperature fluctuations) and then recrystallization of the fat which sometimes migrates to the surface. Although tempering, the formation of stable crystals via a commonly used cooling and slow heating process, can help in retarding bloom, bloom remains a recurring problem in the chocolate confection industry.

Surprisingly, it has been found that, though many of the crystal modifying fats such as acetodistearin exhibit bloom, the diacetin fats do not, nor do this invention's blends of diacetin fats with crystal modifying fats. Thus, chocolate-like confectionery products prepared with the modified diacetin fats of this invention do not exhibit visually apparent bloom after at least six months on the shelf. Moreover, especially preferred confections can withstand fluctuations in temperature that usually give rise to bloom in ordinary chocolate confections even when the modified diacetin fat coating has been quench cooled during manufacture.

Confectionery coatings made with the modified diacetin fats of this invention ordinarily contain a sweetener and a flavoring in addition to the fat component. The sweetener can be a natural sweetener such as a sugar, primarily sucrose, glucose, fructose, and maltose, honey, or any one of known artifical sweeteners including 1-aspartyl-1-phenylalanine methyl ester (commercially available as aspartame or Nutri-Sweet TM), saccharine, cyclamate and the potassium salt of 6-methyl-3,4-dihydrol,1,2,3-oxathiazin-4-one-2,2-dioxide (commercially available as acesulfame-K), or a mixture of these.

Among the preferred reduced calorie confectionery coatings prepared using the modified diacetin fats of this invention are those employing little or no sucrose. Because many artificial sweeteners are substantially sweeter than sucrose, a bulking agent such as polydextrose, isomalt, isomaltulose, polyglucose, polymaltose, carboxymethyl-cellulose, microcrystalline cellulose, cellulose gel, arabinogalactan, as well as mixtures or combinations of any of these is generally employed. These agents can be included in amounts readily determinable by the skilled artisan.

Confectionery coating compositions made with the modified diacetin fats of this invention comprise a flavor in addition to the fat component in amounts effective to deliver flavor to the product. Any type of flavor may be employed, including, for example, chocolate, mint, nut, fruit (including coconut), spices such as cinnamon and vanilla, coffee, maple, honey, molasses, and the like.

For chocolate and chocolate-like compositions, the source of chocolate flavor may be cocoa powder, cocoa butter, chocolate liquor, or the like. Preferably, the source of chocolate is present in an amount of about 5% to about 40% by weight, more preferably about 10% to about 35%, most preferably about 25% to about 35% by weight. Most commonly, cocoa powder, which is usually formed from the press cake remaining after pressing chocolate liquor, such as by grinding the cake first through a coarse tooth roller and then through a finer grind into the desired powder, is utilized. When white chocolate is desired, though, cocoa powder can be eliminated, and the desired chocolate flavor provided by using cocoa butter in the composition. An advantage of the invention is that cocoa butter is miscible in modified diacetin fat in all proportions.

Confectionery coating compositions made using the modified diacetin fats of this invention can also contain other ingredients depending upon the flavor or other properties desired. For instance, milk or milk powders or solids (preferably nonfat) can be included, as can eggs, gelatin, cornstarch or other starch such as potato or rice, fruits and nuts, molasses, and colorings. Lecithin at a level of about 0.5% lowers the viscosity of the coating and facilitates enrobing; other emulsifiers may be employed. Sorbitan fatty acid esters such as sorbitan tristearate used at levels, for example, of about 1 to about 10 weight percent, more narrowly about 1.5 to about 4 weight percent can be added to increase the hardness of the coatings. Example coatings are illustrated in the next section.

Coatings prepared with the modified diacetin fats of this invention exhibit a number of desirable characteristics. With crystal modifier levels of about 10% to about 20%, the modified diacetin fats exhibit surprisingly good snap that rubbery unmodified diacetin fats do not have, yet the compositions are sufficiently hard to be used as confectionery coatings. The compositions have a pleasant crunchy texture, and also surprisingly exhibit a gloss not observed in compositions containing unmodified diacetin fats.

Furthermore, confectionery compositions containing modified diacetin fats exhibit a lower viscosity than diacetin fats, which facilitates pouring the modified fats into molds, and this is achieved without adding lecithin. Yet, on cooling, modified diacetin fats demold much more easily than unmodified diacetin fats.

As has been mentioned, another advantage of the invention is that chocolate and chocolate-like confectionery coatings made using the modified diacetin fats of this invention do not bloom under ordinary circumstances, which increases the shelf life of products made using them. Moreover, the fat does not require tempering. Indeed, modified diacetin fats can be quench cooled without afterwards exhibiting bloom, and this can greatly simplify the manufacture of confections in commercial applications. Modified diacetin fats also set up fast, which simplifies the cooling and hardening step in the manufacture of coated products.

On the other hand, at levels of less than about 10% crystal modifier, modified diacetin fats do not bloom, but they exhibit inferior snap, gloss, hardness and ease of demolding. At levels of more than about 16% to 20% crystal modifier, modified diacetin fats tend to become waxy and have a tendency to bloom, but they demold readily and are quite glossy.

Another advantage of the invention is that desirable organoleptic characteristics can be achieved in coatings formulated with diacetin fats containing about 10% to about 16% crystal modifier. In preferred embodiments, coatings melt away pleasantly in the mouth without leaving a waxy mouthfeel, even after many months on the shelf.

Another advantage of the invention is that preferred modified diacetin fats are low in calories and contain little lauric, myristic, and/or palmitic acid or trans unsaturation, which have recently investigated regarding effects on cholesterol concentrations in blood serum (Bonanome, A., and Grundy, S. M., New Eng. Jour. Med. 318: 1244–1248 (1988) and Mensink, R. P., and Katan, M. B., New Eng. Jour. Med., 323: 439–445 (1990)).

EXAMPLES

The following examples are presented to further illustrate and explain the present invention and should not be taken as limiting in any regard. Unless otherwise indicated, all parts and percentages are by weight, and are based on the weight at the particular stage of the processing being described.

Nuclear magnetic resonance (NMR) data reported are proton NMR data. Fat product analysis also employs supercritical fluid chromatography (SFC), separating and quantifying the mixture components, using a standard procedure. After filtering through a 0.45 micron filter, 0.1 µl of a 30 to 50 mg/ml sample is injected onto a 1×100 mm Deltabond Cyano TM column from Keystone Scientific in a Suprex Model 200A S.C.C. having an S.C.C.-grade carbon dioxide mobile phase and an oven temperature of 125° C. A linear pressure gradient of 100 to 300 atmospheres is applied over a course of 20 minutes (i.e., 10 atm/min), followed by a hold at 300 atmospheres for 10 minutes. A flame ionization detector at 400° C. detects emerging mixture components run against an internal standard of methyl tetradecanoate (10 to 12 mg/mL) in methylene chloride. External standards of mono-, di-, and tristearin (~10 mg/mL each) are run under identical conditions. Using these peak areas, the peak areas of the sample are normalized, added together, and divided by the total to obtain percentages of fat components.

Differential scanning calorimetry (DSC) is used to obtain information about the melting and crystallization behavior of the fats and solids content at any given temperature. A sample is cooled from about 20° C. above its melting point to about 20° C. below, held at the final temperature, and then reheated to the initial temperature. Crystallization and melting thermograms are subjected to several analyses. The melting point(s) are taken as the peak minima (endothermic transition in the down direction of the chart plotting mW per unit time versus temperature) obtained in the heating cycle, and the crystallization temperature as the peak onset in the cooling cycle. Enthalpies of phase transitions are automatically calculated in mJoules/mg of sample by choosing the two temperature points of onset of melting and 100% melted. Percent solids, i.e., the percent liquid portion of the sample at any given temperature, are calculated by integration.

Unless otherwise indicated, solid fat indices (herein abbreviated S.F.I.) are determined using dilatometry according to A.O.C.S. Method Cd 10-57 (1989), reporting solids at 50° F. (10° C.), 70° F. (21.1° C.), 80° F. (26.7° C.), 92° F. (33.3° C.), and 100° F. (37.8° C.). Solid fat contents (S.F.C.) of the products are determined by NMR using A.O.C.S. method 16-81 (1989). Mettler dropping points (M.D.P.) are determined using a Mettler Thermosystem FP 800 following A.O.C.S. Method Cc 18-80 (1989).

EXAMPLE 1

This example illustrates the preparations of diacetostearin and several diacetostearin crystal modifiers.

Diacetostearin is prepared by reacting monostearin with acetic anhydride. A reaction flask equipped with a magnetic stirrer, heating mantle, thermometer, and reflux condenser is charged with 968.22 g (2.7 moles) 1-glycerol-rac-monostearin obtained from Spectrum Chemicals (Lot #FC027), which is melted prior to adding 578.9 g (5.67 moles) acetic anhydride (99%, Aldrich Chemicals). The reaction flask is heated to reflux for 8 hours until the reaction mixture is a golden liquid at room temperature, and the acetic acid side product is removed by vacuum distillation. The yield of distillate is quantitative. The product is passed through a falling film still and deodorized (40 mL water, <1 mm Hg, 180° to 200° C.). The yield is 1200 g (2.1 moles) of a golden yellow wax. Fatty acid analysis shows the product to have 66% acetic acid residues and 34% stearic acid residues. This diacetostearin is employed in the next example.

To prepare acetodistearin, a distearin starting material is first prepared. A 3-L, 2-neck reaction flask equipped with a heating mantle, thermometer, stirrer, and reflux condenser is charged with 248 g stearic anhydride (0.45 moles, obtained from Aldrich) and 37 g glycidol (0.5 moles). The mixture is stirred and heated to 95°–100° C. for 3 hours, 3.2 g tetraethylammonium bromide is added, and the mixture stirred and heated for another 3 hours at 100°–105° C. DL-2-amino-1-propanol (2.4 g) is added and the flask is cooled until it solidifies (~65° C.). The reaction flask is placed in a 60°–65° C. oven, held for 48 hours, and then heated to melt the product for transfer into a 4-L beaker. The product is crystallized from acetone, washed and dried. An 85% yield of a >93% pure product is obtained.

A 3-L, 3-neck reaction flask equipped with a heating mantle, stirrer, thermometer and reflux condenser is charged with 502 g (0.8 mole) of the distearin starting material. This is melted, 82 g acetic anhydride (0.8 mole +a 5% excess, ~99% pure, obtained from Aldrich Chemicals) is added, and the mixture is refluxed for 8 hours, producing a white solid at room temperature. The product is vacuum distilled to remove acetic acid, passed through a falling film still (164° to 168° C., <1 mm Hg to remove volatiles) and deodorized (180° to 200° C., 50 mL water, <1 mm Hg). Fatty acid analysis shows this product to have 31% acetic acid residues and 69% stearic acid residues. This acetodistearin is employed in the next example.

Alternatively, acetodistearin is prepared by adding 5 mL acetyl chloride to 90 mg (0.14 moles) 1,3-distearin, and stirring and heating the mixture to 85° C. until all the acetyl chloride is reacted. An additional 2 mL acetyl chloride is added and the mixture is reheated to yield predominantly 2-acetyl-1,3-distearoyl glyceride. Similarly, a mixture of 2.1 g (0.01 mole) stearoyl chloride and 1.4 g (0.01 mole) monoacetin obtained from Kodak is heated to 85° C. for 2 hours, another 4.0 g stearoyl chloride is added, and the mixture is reheated to yield predominantly 1-acetyl-2,3-distearoyl glyceride.

Propiodistearin is prepared by reacting a 1:1 molar ratio of distearin with propionic anhydride. A 2-L, 2-neck flask equipped with a thermometer, reflux condenser, heating mantle and stirrer is charged with 367 g distearin, which is melted prior to adding 76 g propionic anhydride. The mixture is refluxed at 125° C. for ~5 hours, left to stand overnight at room temperature, and refluxed with stirring at 80° C. for 6 hours. The mixture is distilled to yield a solid crude product that is dissolved in hexane and washed with water until neutral. Hexane is removed in vacuuo and the off-white product solid, dried. The yield is 374 g (93%).

Butyrodistearin is prepared by reacting distearin with butyric anhydride (~99% pure, obtained from Aldrich). A 3-L, 3-neck flask equipped with a thermometer, reflux condenser, heating mantle and stirrer is charged with 720 g distearin, which is half melted prior to adding 204 mL butyric anhydride. The mixture is heated for ~2½ hours at 85° C., left to stand without heat for two days, and refluxed at 85° C. for 8 hours. The mixture is distilled twice at 1 mm Hg to yield 743 g (93%) of a hard, light brown solid.

EXAMPLE 2

This example compares and contrasts diacetostearin chocolate coatings containing different levels of acetodistearin, and comparisons of these with control chocolate coatings containing tempered cocoa butter.

The coatings are prepared by mixing equal parts confectioner's sugar, cocoa powder, and fat thoroughly at 55° to 65° C. The mixture is then poured into molds and allowed to cool to ambient temperature or refrigerated. The coatings are then stored at 24° C.

FIG. 1 shows the solid fat content on the day of preparation of the diacetostearin coatings containing three levels of acetodistearin: 2% (---△---), 13% (·····⊙·····), and 30% (- — — —) compared with tempered cocoa butter (—□—).

Figure 2:
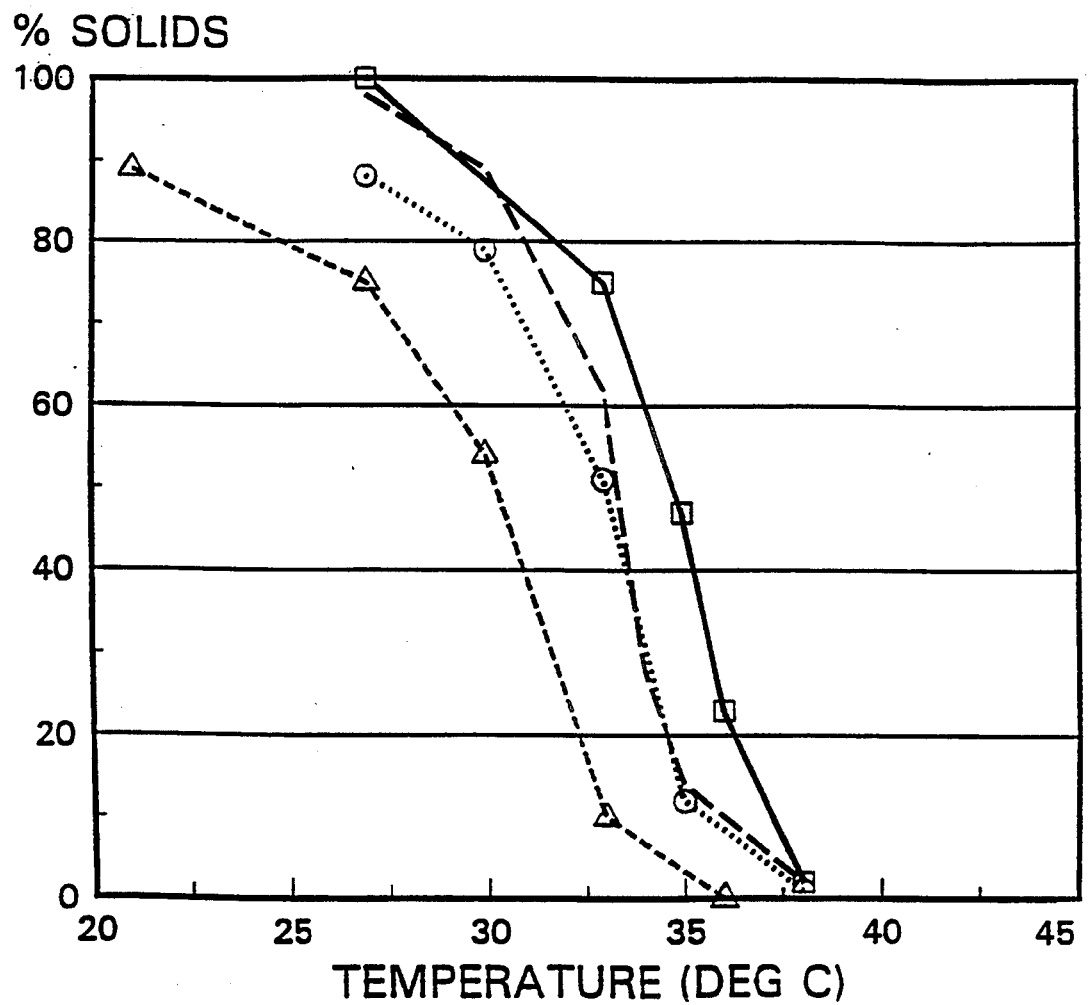
FIG. 2 shows DSC solid fat indices of chocolate coating compositions prepared using diacetostearin containing 2% acetodistearin freshly prepared (---△---), after storage 2 weeks at 24° C. (·····⊙·····), and after storage 2 months at 24° C. (-- -- --), compared with a control coating prepared using tempered cocoa butter (----☐----). The coating exhibits softness and pliability, and changes only slightly after a year's storage.

The DSC melting profile of coating prepared using cocoa butter (—□—) is compared with a sample coating prepared using diacetostearin containing 2% acetodistearin in Figure 2. Freshly prepared (---△---), the sample coating is softer than the cocoa butter control. The coating has an acceptable, though somewhat too soft, mouthfeel. After storage for two weeks, the melting profile exhibits a slight change (·····⊙·····), which remains relatively stable for two months (- — — —) to a year. The coating remains slightly too soft, pliable, bendable and rubbery.

Figure 3:
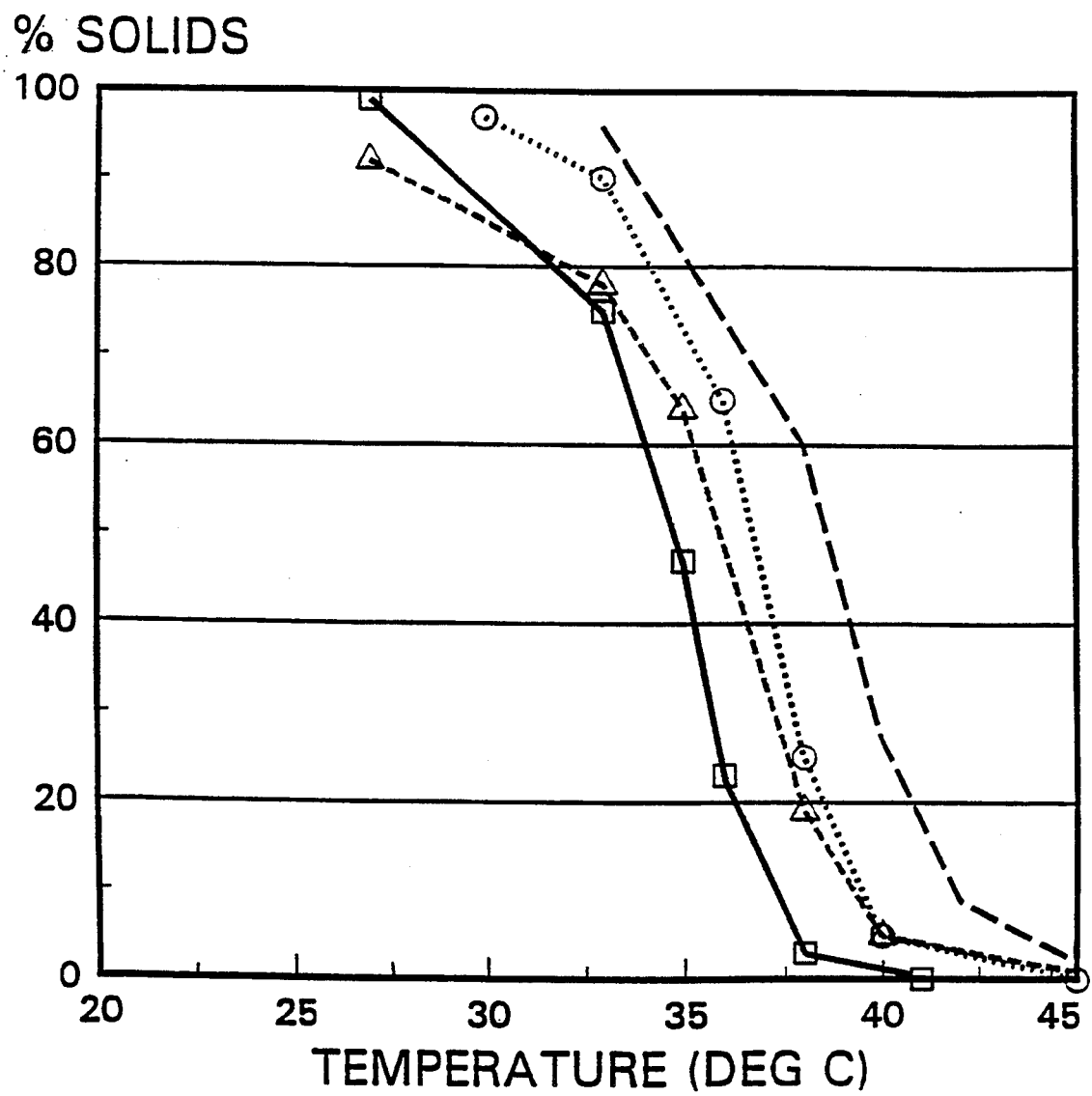
FIG. 3 shows DSC solid fat indices of chocolate coating compositions prepared using diacetostearin containing 30% acetodistearin freshly made (---△---), after storage 2 days at 24° C. (·····⊙·····), and after storage 4 days at 24° C. (-- -- --), compared with a control coating prepared using tempered cocoa butter (----☐----). Freshly prepared coatings exhibit waxiness, and within a few days at room temperature, the waxiness increases.
Figure 4:
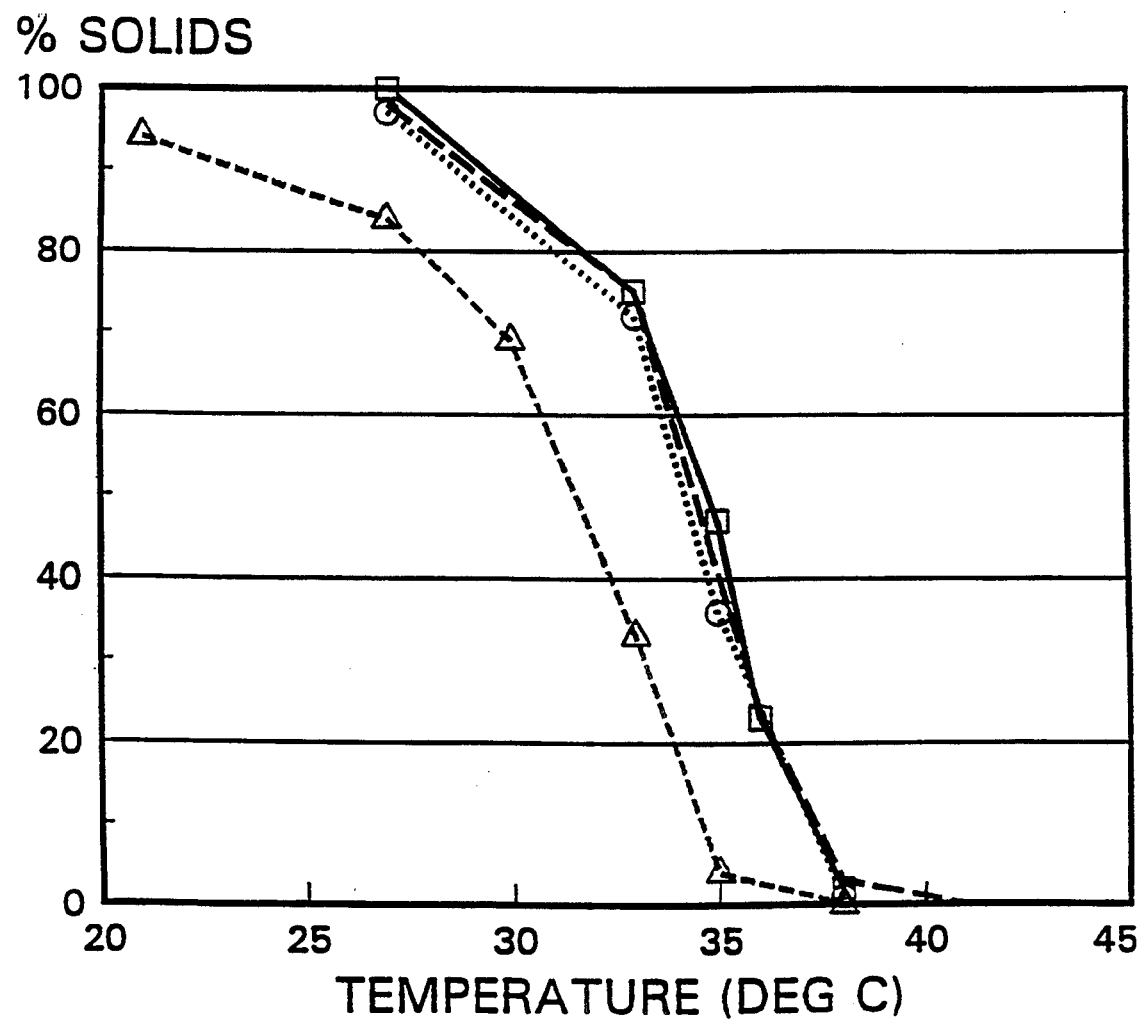
FIG. 4 shows DSC solid fat indices of chocolate coating compositions prepared using diacetostearin containing 13% acetodistearin freshly made (---△---), after storage 10 weeks at 24° C. (·····⊙·····), and after storage 4 months at 24° C. (-- -- --), compared with a control coating prepared using tempered cocoa butter (----☐----). The coating hardens over a period of weeks to a state closely resembling tempered cocoa butter, and exhibits good snap, hardness and improved mold release in comparison with coatings prepared with 3% acetodistearin.

FIG. 3 demonstrates the change in solid fat content with time for a chocolate coating containing 30% acetodistearin and 70% diacetostearin, compared with a cocoa butter control coating (—□—). When newly prepared (---△---), it exhibits a somewhat too waxy mouthfeel. Within a few days at room temperature, it becomes very waxy (·····⊙·····) at 2 days; (- — — —) at 4 days). Thus, levels of 30% are too high for ambient shelf stored products. However, the level is satisfactory for some refrigerated products because at these levels of acetodistearin in diacetostearin, the changes to harder fat crystal forms are slowed in the refrigerator.

The solid fat content profile and changes with time for a coating containing, instead, 13% acetodistearin and 87% diacetostearin, exhibits an acceptable mouthfeel freshly prepared (---△---). Over a period of several weeks, it hardens to a state closer to cocoa butter (·····⊙·····) at 10 weeks), and remains stable in this state (- — — —) at 4 months). The chocolate exhibits better snap, hardness, and improved mold release compared with the 3% sample.

A confectioner's coating exhibiting good properties is also prepared by thoroughly combining equal parts confectioner's sugar, cocoa powder and a mixture of 13% acetodistearin and 87% diacetostearin at 55° to 65° C., adding 0.5% by weight lecithin, and cooling.

EXAMPLE 3

This example further compares and contrasts the physical properties of diacetostearin with diacetostearin containing crystal modifiers.

Using a Brookfield viscometer at 41.5° C., pure diaceto-stearin is very thick and does not flow, exhibiting a viscosity of 16.4 centipoise. A mixture of 12.5% acetodistearin in diacetostearin flows more, exhibiting a viscosity of 8.1 centipoise. A mixture of 25% acetodistearin and 75% diacetostearin flows readily and exhibited a viscosity of 4.1 centipoise.

Chocolate bars having identical dimensions are prepared by mixing 1 part confectioner's sugar, 1 part cocoa, and 1 part of these test fats (diacetostearin, 12.6% acetodistearin in diacetostearin, and 25% acetodistearin in diacetostearin). The chocolates are subjected to rheological measurements using an Instron TM 4501 equipped with a Series IX automated Materials Testing System 1.15 (obtained from Instron Corporation, 100 Royall St., Canton, Mass. 02021). Puncture and three point bend tests that compare and contrast measurements of a standard force directed as a probe or blade against the samples as a function of time, the applied load per unit of cross section against an increase in length per unit length, and stress versus strain are run.

Figure 5A:
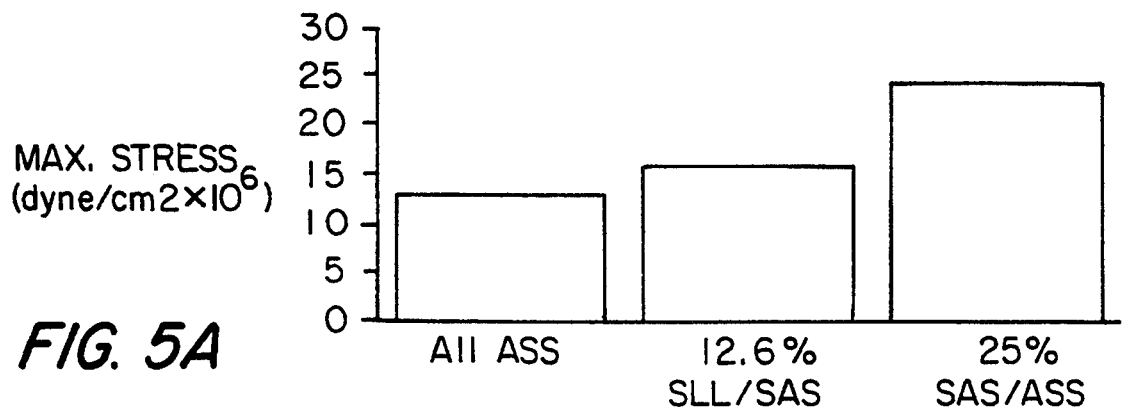
FIG. 5 shows Instron ™ puncture (A, maximum stress in dyne/cm$^2 \times 10^6$) and three point bend (B, maximum stress and C, Young Modulus in dyne/cm$^2 \times 10^6$) data on chocolate bars formulated with diacetin fat (AAs), diacetin containing 12.6% acetodistearin, and diacetin containing 25% acetodistearin.
Figure 5B:
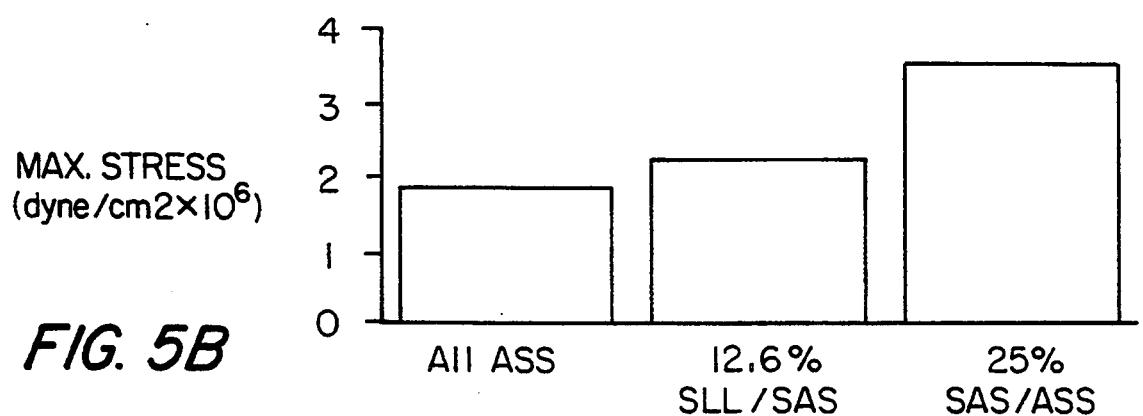
Figure 5C:
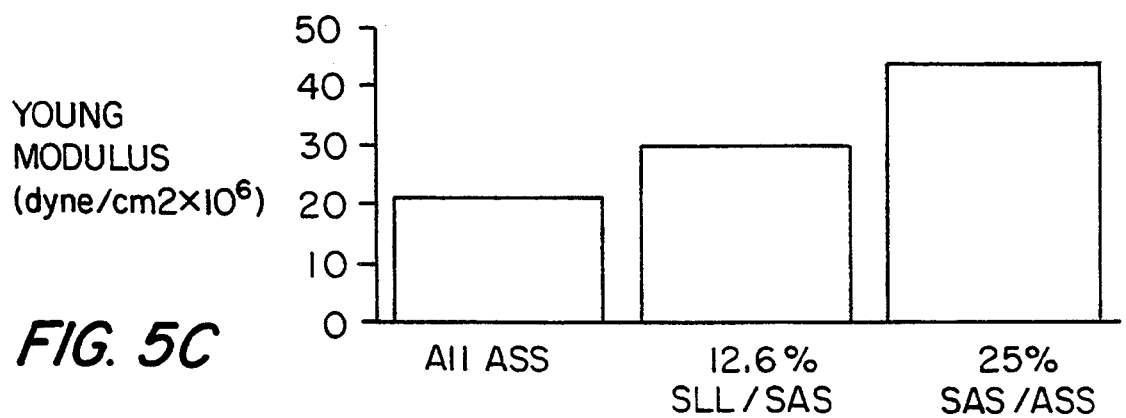

The puncture tests are run using a 1.6 mm probe at 50 mm/min at 73° F. and 50% humidity. Fifteen data points are collected per sample, and the maximum stress (dyne/cm$^2$ × 10$^6$) for each sample is averaged. Three point bend tests are run in triplicate at 50 mm/min at 73° F. and 50% humidity for each sample using the same equipment and a 69.49 mm × 2.81 mm blade descending on a platform having a 3.0 cm spacing between bars. The average maximum stress (dyne/cm$^2$ × 10$^6$) is plotted in FIG. 5 (A summarizes puncture test data; B, three point bend test data).

Plots of load versus displacement and data on stress and Young's moduli (C summarizes three point bend test data) illustrate that diacetostearin exhibits more elasticity than the other samples containing crystal modifiers. The samples do not show a steep slope to a sharp peak expected for a material undergoing brittle fracture. Instead, the material deforms with the applied load (see FIG. 5). The material behaves like a plastic material where deformation or flow occurs, and so the chocolate bars exhibit no snap.

In contrast to this, chocolates made diacetostearin containing crystal modifiers have a steeper slope and sharper peak than the diacetostearin samples. The stress at failure, which is related to the peak load, and the Young's modulus, which is related to the slope of the curve, illustrate the differences. The values are higher. The samples containing crystal modifiers undergo brittle fracture rather than deforming under an applied load, and hence exhibit snap not observed with diacetin.

EXAMPLE 4

This example illustrates how improved acetoglycerides of this invention can be prepared using interesterification.

Diacetostearin containing crystal modifiers are prepared by reacting 1 mole fully hydrogenated soybean oil (obtained from Vandenberg Food Ingredient Group, Lisle, Ill.) with 12 moles triacetin (obtained from Aldrich Chemical Company, Milwaukee, Wisc.). The reactants are blended and heated to 115° C. and interesterified in the presence of 0.4% sodium methoxide by heating with agitation under a vacuum for about 10 minutes. The reaction is stopped and the mixture cooled, washed, bleached, dried and filtered to yield a product having a M.D.P. of 31.2° C. This is further purified by steam deodorization at 210° C. for 2 hours to yield a solid product having a M.D.P. of 35.7° C. and an S.F.C. of 90.6% at 32° F., 89.0% at 50° F., 87.0% at 70° F., 83.9% at 80° F., 37.4% at 92° F., 1.0% at 100° F., and 0% at 104° F.

Another improved acetoglyceride fat of this invention is prepared by interesterifying 1 mole hydrogenated canola (refined, low erucic rapeseed oil containing 4% palmitic acid, hydrogenated at 180° C. and 60 lbs hydrogen until the Iodine Value (IV) is ≦3) with 8 moles triacetin using the procedure described above and steam deodorizing to yield a product having a M.D.P. of 36.1° C. and a S.F.I. of 69.7% at 50° F., 67.4% at 70° F., 63.1% at 80° F., 29.6% at 92° F., and 0 at 100° F. Another sample is prepared by interesterifying 1 mole of hydrogenated high erucic rapeseed oil (obtained from CSP) with 1.5 moles triacetin in the presence of 0.3% sodium methoxide and steam deodorizing to yield a product having a M.D.P. of 50° C.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

We claim:

1. A coating composition having an acetoglyceride fat ingredient comprising a mixture of
   (a) about 70% to about 95% of a diacetin fat comprising triglycerides bearing two acetic acid residues and one long, saturated $C_{16}$ to $C_{22}$ fatty acid residue per molecule; and
   (b) about 5% to about 30% of a crystal-modifying fat comprising triglycerides bearing one short $C_2$ to $C_4$ acid residue and two long, saturated $C_{16}$ to $C_{24}$ fatty acid residues per molecule added to the diacetin fat in amounts effective to impart snap to the composition so that the composition undergoes brittle fracture rather than deforming under an applied load.

2. A composition according to claim 1 wherein the crystal modifying fat is selected from the group consisting of acetodistearin, propiodistearin, butyrodistearin, and mixtures of these.

3. A composition according to claim 2 wherein at least about 85% of the diacetin fat is diacetostearin.

4. A composition according to claim 3 wherein the crystal modifying fat comprises acetodistearin.

5. A confectionery composition according to claim 4 further comprising a chocolate flavor and a sweetener.

6. A composition according to claim 1 wherein the fat ingredient comprises a mixture of about 83% to about 90% diacetin fat and about 10% to about 16% crystal modifying fat.

7. A composition according to claim 6 wherein the fat ingredient comprises a mixture of about 87% diacetin fat and about 13% acetodistearin.

8. A confectionery coating composition comprising a coating composition according to claim 1.

9. A composition according to claim 8 wherein the coating composition comprises from about 10% to about 20% crystal modifying fat.

10. A composition according to claim 9 wherein the coating composition comprises from about 10% to about 18% crystal modifying fat.

11. A composition according to claim 10 wherein the coating composition comprises from about 10% to about 16% crystal modifying fat.

12. In a confectionery coating composition comprising a sweetener, a flavor, and a diacetin fat ingredient selected from the group consisting of diacetopalmitin, diacetostearin, diacetoarachidin, diacetobehenin, and mixtures thereof, an improvement wherein the diacetin fat ingredient further comprises about 10 to about 18% of a crystal modifier comprising triglycerides bearing one $C_2$ to $C_4$ acid residue and two saturated $C_{16}$ to $C_{22}$ fatty acid residues per molecule such that the coating composition containing crystal modifier exhibits snap and undergoes brittle fracture rather than exhibiting plasticity and deforming under an applied load like a diacetin fat.

13. An improvement according to claim 12 wherein the diacetin fat comprises diacetostearin and the crystal modifier comprises acetodistearin.

14. An improvement according to claim 13 wherein the flavor is chocolate.

15. An improvement according to claim 13 wherein said crystal modifier further comprises sorbitan tristearate.

16. A confectionery coating composition comprising a sweetener, a flavor and a fat ingredient, wherein the fat ingredient comprises a mixture of about 84% to about 90% diacetostearin and about 10 to about 16% acetodistearin.

17. A composition according to claim 16 comprising about 87% diacetostearin and about 13% acetodistearin.

18. A method for improving the crystal properties of a saturated diacetin coating fat comprising incorporating into said diacetin coating fat from about 10 to about 16% of a crystal modifier comprising triglycerides bearing one $C_2$ to $C_4$ acid residue and two saturated $C_{16}$ to $C_{22}$ fatty acid residues.

19. A method according to claim 18 wherein the saturated diacetin coating fat is selected from the group consisting of diacetopalmitin, diacetostearin, diacetoarachidin, diacetobehenin, and mixtures of these.

20. A method according to claim 19 wherein the crystal modifier is selected from the group consisting of acetodistearin, propiodistearin, butyrodistearin, and mixtures of these.

21. A method according to claim 20 wherein the diacetin coating fat is predominantly diacetostearin and the crystal modifier comprises acetodistearin.

22. A method according to claim 21 wherein the diacetin coating fat contains about 13% crystal modifier.

23. A method according to claim 19 wherein the diacetin coating fat further comprises about 1.5 to about 4% sorbitan fatty acid ester.

24. A method according to claim 23 wherein the sorbitan fatty acid ester is sorbitan tristearate.

* * * * *